United States Patent [19]

Massonne et al.

[11] Patent Number: 5,502,188

[45] Date of Patent: Mar. 26, 1996

[54] PRODUCTION OF ALMOST COLORLESS SOLUTIONS OF N-METHYLMORPHOLINE OXIDE

[75] Inventors: Klemens Massonne, Westheim; Gerd Konrad, Limburgerhof, both of Germany; Mark D. Sandison, Dearborn, Mich.; Gregory E. Moffitt; Lawrence E. James, both of Grosse Ile, Mich.; John Banger, High Bridge, N.J.

[73] Assignee: BASF Corporation, Mount Olive, N.J.

[21] Appl. No.: 482,391

[22] Filed: Jun. 7, 1995

[51] Int. Cl.⁶ ................................................. C07D 295/24
[52] U.S. Cl. ............................................. 544/173; 203/13
[58] Field of Search ............................... 544/173; 203/14

[56] References Cited

U.S. PATENT DOCUMENTS

| | | | |
|---|---|---|---|
| 4,247,480 | 1/1981 | Marata et al. | 564/298 |
| 4,748,241 | 5/1988 | Scholten et al. | 544/173 |
| 4,942,260 | 7/1990 | Laurenzo | 544/173 |
| 4,970,341 | 11/1990 | Summerford | 564/298 |
| 4,994,614 | 2/1991 | Bauer | 564/300 |
| 5,055,233 | 10/1991 | Borland et al. | 252/547 |
| 5,075,501 | 12/1991 | Borland et al. | 564/297 |
| 5,130,488 | 7/1992 | Smith et al. | 564/298 |

FOREIGN PATENT DOCUMENTS

| | | |
|---|---|---|
| 0307184 | 3/1989 | European Pat. Off. |
| 0320694 | 6/1989 | European Pat. Off. |
| 0356918 | 3/1990 | European Pat. Off. |
| 0401503 | 12/1990 | European Pat. Off. |
| 0424965 | 5/1991 | European Pat. Off. |
| 0426084 | 5/1991 | European Pat. Off. |
| 0498346 | 3/1992 | European Pat. Off. |
| 0553552 | 8/1993 | European Pat. Off. |
| 2632638 | 6/1988 | France . |
| 3618352 | 12/1987 | Germany . |

*Primary Examiner*—Robert W. Ramsuer
*Attorney, Agent, or Firm*—Joanne P. Will

[57] ABSTRACT

Aqueous solutions of N-methylmorpholine N-oxide having color numbers below 200 APHA, based on an N-methylmorpholine N-oxide content of 50% by weight, are produced by reacting aqueous hydrogen peroxide solutions with aqueous solutions of N-methylmorpholine having a water content of at least 35% by weight.

7 Claims, No Drawings

PRODUCTION OF ALMOST COLORLESS SOLUTIONS OF N-METHYLMORPHOLINE OXIDE

FIELD OF INVENTION

The present invention relates to a process for producing N-methylmorpholine N-oxide (NMMO) by oxidation of N-methylmorpholine (NMM) with hydrogen peroxide using dilute aqueous starting solutions of N-methylmorpholine with a water content of at least 35% by weight as initial charge.

BACKGROUND

N-Methylmorpholine oxide is a proven solvent for cellulose for the production of cellulose fibers, e.g. U.S. Pat. No. 3,447,939. It is further used as an oxidizing agent in the dihydroxylation of olefins, See, Sharpless et al., J. Am. Chem. Soc. 98 [1976], 1986 and finds utility in intermediate production for pharmaceuticals. The preferred commercial form is an aqueous solution from 50 to 60% in strength.

N-Methylmorpholine oxide, or tertiary amine oxides, in general, are prepared by oxidizing the corresponding amines with hydrogen peroxide, as described in EP 553 552, U.S. Pat. No. 4,247,480, EP 426 084, FR 26 32 638, EP 401 503, U.S. Pat. Nos. 5,055,233, 5,075,501, 5,130,488, EP 307 184, U.S. Pat. No. 4,994,614, EP 320 694, EP 356 918, DE 36 18 352, U.S. Pat. No. 4,748,241, EP 498 346, EP 424 965, U.S. Pat. No. 4,970,341, incorporated by reference herein.

The general reaction scheme for the preparation of NMMO is:

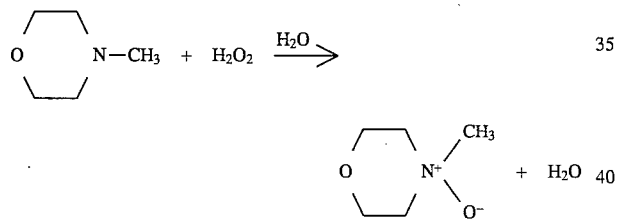

Nitrosamines and colored species are reaction byproducts which negatively impact product quality, even in low concentrations. Nitrosamines are undesirable even in trace amounts because of their carcinogenicity and much effort has been devoted to the suppression of nitrosamine formation, e.g. EP 553 552, U.S. Pat. Nos. 4,247,480, 4,994,614, EP 356 918. However, little attention has been paid to the formation of the colored species when the N-methylmorpholine is oxidized with hydrogen peroxide in the presence of an inert gas or a carbon dioxide atmosphere.

According to U.S. Pat. No. 4,748,241, the color of the resulting NMMO solution can be reduced from "deeply yellow-brown" to "slightly tinged yellow" by purifying the N-methylmorpholine by an azeotropic distillation with water. The reaction of the NMM-water azeotrope (74.5% NMM, 25.5% water) with aqueous 30–65% hydrogen peroxide is said to lead only to slightly yellowish NMMO solutions.

The reaction of undiluted NMM-water azeotrope with 30–65% aqueous hydrogen peroxide is illustrated in Examples 1–8. The NMMO solutions obtained from Examples 1–8 all had APHA color numbers above 350 units and are not suitable for all applications unless further purification steps are undertaken. The APHA color number is a standard method based on a visual comparison of the sample with solutions with known concentrations of cobalt chloroplatinate. The unit of color is that produced by 1 mg platinum/L in the form of the chloroplatinate ion.

Applicants' invention represents an improvement over the art because the reaction of hydrogen peroxide with NMM azeotrope (about 26% water) results in highly colored NMMO solutions as illustrated in Examples 1–8. Surprisingly, Applicants have reduced the color of the NMMO solution by increasing the water content of the NMM solution to at least 35% prior to the addition of hydrogen peroxide. Examples 9–23 are illustrative of the Applicants' invention and its superiority over the art.

SUMMARY

1. A process for producing aqueous solutions of N-methylmorpholine N-oxide having APHA numbers below 200, based on an N-methylmorpholine N-oxide content of 50% by weight, comprising the steps of:

A. obtaining an aqueous N-methylmorpholine solution whose water content is at least 35% by weight;

B. oxidizing the aqueous N-methylmorpholine solution with hydrogen peroxide at a temperature range from 50°–80° C.;

C. adjusting the concentration of the aqueous N-methylmorpholine N-oxide solution prepared in (B) by distilling off residual N-methylmorpholine and water.

DETAILED DESCRIPTION

A process for producing aqueous solutions of N-methylmorpholine N-oxide having color numbers below 200 APHA, based on an N-methylmorpholine N-oxide content of 50% by weight, comprising the steps of: a) oxidizing aqueous N-methylmorpholine, whose water content is at least 35% by wt. with aqueous hydrogen peroxide at a temperature of 50°–80° C.; b) adjusting the concentration of the N-methylmorpholine solution prepared in (a) by distilling off the unconverted N-methylmorpholine.

Specifically, aqueous solutions of N-methylmorpholine N-oxide having color numbers below 200 APHA, based on an N-methylmorpholine N-oxide content of 50% by weight, are produced by reacting N-methylmorpholine with aqueous hydrogen peroxide solution at temperatures from 50° to 80° C., preferably 65° C. –70° C., more preferably 65°, in a conventional manner, which comprises performing the oxidation of NMM by introducing the aqueous hydrogen peroxide solution into an aqueous solution of N-methylmorpholine whose water content is at least 35% by weight, based on the N-methylmorpholine solution, at the start of the oxidation. After the oxidation reaction has ended, the resulting solution is adjusted to the desired concentration of N-methylmorpholine N-oxide by distilling off unconverted N-methylmorpholine and water.

Further, the starting material used is distilled N-methylmorpholine and preferably the steam distillation azeotrope of N-methylmorpholine/water whose preparation is described in U.S. Pat. No. 4,748,241 incorporated by reference herein.

Next, the N-methylmorpholine or the said azeotrope is admixed with sufficient water to achieve at least the required water concentration of 35% by weight. There are no upper limits for the dilution, but practical considerations dictate that a limit of 60% by weight of water will generally not be exceeded.

The concentration of the hydrogen peroxide solution can vary over a wide range. Typically, however, the hydrogen peroxide solution used will be from 30 to 65% in strength, preferably 50%.

After the said stated water addition, not only the reaction temperature but also the metering rate of the hydrogen peroxide and the molar ratio of NMM: $H_2O_2$ can be varied within wide limits without incurring a deeper discoloration of the product solutions. Preference is given to reaction temperatures within the range from 50° to 80° C., metering rates of from 100% to 6%/hour of the total amount (based on 100% $H_2O_2$) for the hydrogen peroxide and molar ratios of N-methylmorpholine to hydrogen peroxide within the range from 1.43:1.0 to 0.90:1.0.

Aqueous hydrogen peroxide solution is metered into the methylmorpholine/water mixture in a conventional manner. The mixture is stirred until the reaction has ended and the concentration of the remaining NMMO solution is set to the desired value by vacuum distillation, if necessary.

As stated hereabove, Examples 1–8 illustrate the difficulties encountered with the prior art process, specifically the high (greater than 350) APHA units.

EXAMPLE 1

A thermostated 1 liter glass vessel equipped with a stirrer and a stillhead is charged with 500 g of N-methylmorpholine/water azeotrope (74.3% of NMM) under an inert gas atmosphere of nitrogen, followed at an internal temperature of 70° C. by the metered addition over 2 h of 249 g of 35% strength hydrogen peroxide. On completion of the addition the mixture was stirred at 68° for a further 6 h. 207 g of an N-methylmorpholine/water mixture were distilled off under a vacuum of 100 mbar to leave 587 g of a 59.8% strength N-methylmorpholine N-oxide solution in water. 115 g of water were added to produce a 50% strength solution. APHA color number=417.

EXAMPLE 2

A thermostated 1 liter glass vessel equipped with a stirrer and a stillhead was charged with 250 g of N-methylmorpholine/water azeotrope (74.3% of NMM) under an inert gas atmosphere of nitrogen, followed at an internal temperature of 70° C. by the metered addition over 2 h of 517 g of 10% strength hydrogen peroxide. On completion of the addition the mixture was stirred at 65°–70° C. for a further 6 h. 459 g of an NMM/water mixture were distilled off under a vacuum of 100 mbar to leave 308 g of a 57.2% strength NMMO solution in water. 44 g of water added to produce a 50% strength solution. APHA color number=404.

EXAMPLES 3 AND 4

A thermostated one liter glass vessel equipped with a stirrer and a stillhead was charged with 402.0 g of N-methylmorpholine/water azeotrope (73.5% of NMM) under an inert gas atmosphere of nitrogen. At an internal temperature of 65° to 66° C. 2.53 mol of aqueous hydrogen peroxide solution were metered in over 16 h (See Table 1 for concentration of $H_2O_2$). On completion of the addition of $H_2O_2$ the mixture was stirred at 65° C. for 5 h. 240 g of an N-methylmorpholine/water mixture were distilled off under a vacuum of 100 mbar to leave a bottom product whose N-methylmorpholine N-oxide content was found by titration with 0.5 mol/l hydrochloric acid and set to 50±0.5% by weight with water. The APHA color number of the solution was determined.

TABLE 1

| Example | Concentration of $H_2O_2$ [% by weight] | Molar ratio of NMM: $H_2O_2$ | End product APHA Color number |
|---------|------------------------------------------|-------------------------------|-------------------------------|
| 3 | 30 | 1.15:1 | 368 |
| 4 | 50 | 1.15:1 | 375 |

EXAMPLES 5 TO 8

A four liter stainless steel reactor was charged with the amount of N-methylmorpholine/water azeotrope (73.5% by weight) indicated in Table 2, followed by the metered addition at 65° C. of the indicated amount of a 50% strength aqueous hydrogen peroxide solution (metering time see Table 2). On completion of the addition the mixture was stirred at 65° C. for 5 hr. The workup and setting of the N-methylmorpholine N-oxide content of 50±0.5% by weight was carried out as in Example 1 and 2. The APHA color number of the end products is reproduced in Table 2.

TABLE 2

| Example | NMM/water azeotrope [g] | 50% strength $H_2O_2$ [g] | Metering time [h] | Molar ratio NMM: $H_2O_2$ | End product APHA color number |
|---------|--------------------------|----------------------------|--------------------|----------------------------|-------------------------------|
| 5 | 2088 | 840 | 16 | 1.23:1 | 385 |
| 6 | 1917 | 840 | 16 | 1.13:1 | 385 |
| 7 | 2002 | 840 | 11 | 1.17:1 | 432 |
| 8 | 2088 | 840 | 6 | 1.23:1 | 424 |

All the solutions obtained in Examples 1–8 had a distinctly yellow color. In terms of the APHA color number, all Examples 1–8 rated above 350 units. These NMMO solutions are not suitable without restrictions for all applications unless they are purified by crystallization.

However, the present invention provides a simple method for reducing the color number of the aqueous NMMO solution by a distinct amount, i.e. to below 200 APHA, based on a 50% strength solution. Examples 9–23 which follow illustrate the utility of the present invention and its superiority over the prior art as illustrated in Examples 1–8. The APHA numbers in Examples 9–23 are below 200 APHA and colorless solutions of NMMO suitable for use without further purification are obtained. The N-methylmorpholine azeotrope used in Examples 9–23 was prepared as described in U.S. Pat. No. 4,748,241 incorporated by reference herein.

EXAMPLES 9 to 14

The oxidation was performed as described in Comparative Examples 3 and 4 and the reaction temperature was varied as indicated in Table 3. In each case the N-methylmorpholine/water azeotrope was diluted with the stated amount of water before the addition of the $H_2O_2$. Workup and adjustment of the content was carried out as indicated in each comparative example.

TABLE 3

| Ex. | NMM/-water azeotrope [g] | $H_2O_2$-solution [g] concentration [% by weight] | $H_2O$ [g] | Reaction temperature [°C.] | End product APHA color number |
|-----|---------------------------|---------------------------------------------------|------------|------------------------------|-------------------------------|
| 9 | 402.0 | 287/30 | 114 | 65 | 119 |

TABLE 3-continued

| Ex. | NMM/-water azeotrope [g] | H₂O₂-solution [g] concentration [% by weight] | H₂O [g] | Reaction temperature [°C.] | End product APHA color number |
|---|---|---|---|---|---|
| 10 | 402.0 | 287/30 | 57 | 65 | 139 |
| 11 | 402.0 | 172/50 | 114 | 65 | 53 |
| 12 | 402.0 | 172/50 | 57 | 65 | 186 |
| 13 | 402.0 | 172/50 | 114 | 60 | 40 |
| 14 | 402.0 | 172/50 | 114 | 75 | 110 |

EXAMPLES 15 TO 20

The runs were carried out as described in Examples 5 to 8 except that prior to the H₂O₂ addition the amount of water indicated in Table 4 was added to the N-methylmorpholine/water azeotrope.

TABLE 4

| Example | NMM/water azeotrope [g] | 50% strength H₂O₂ [g] | Water added [g] | Metering time [h] | Molar ratio of NMM:H₂O₂ | End product APHA color number |
|---|---|---|---|---|---|---|
| 15 | 1775 | 714 | 693 | 16 | 1.23:1 | 135 |
| 16 | 1775 | 714 | 693 | 6 | 1.23:1 | 80 |
| 17 | 1725 | 756 | 643 | 6 | 1.13:1 | 100 |
| 18 | 2002 | 840 | 355 | 16 | 1.17:1 | 180 |
| 19 | 2002 | 840 | 355 | 11 | 1.17:1 | 130 |
| 20 | 1917 | 840 | 320 | 11 | 1.12:1 | 135 |

EXAMPLES 21 AND 22

Procedures and workup were carried out as in Examples 9 to 14. The molar ratio of $H_2O_2$:NMM and the metering time were varied as indicated in Table 5.

TABLE 5

| Example | NMM/water azeotrope [g] | H₂O₂ solution 50% strength by weight [g] | Water added [g] | Reaction temperature [°C.] | Molar ratio of NMM: H₂O₂ | Metering time [h] | End product APHA color number |
|---|---|---|---|---|---|---|---|
| 21 | 402 | 194,5 | 114 | 65 | 1.02:1 | 16.5 | 80 |
| 22 | 402 | 194,5 | 114 | 65 | 1.02:1 | 3 | 53 |

EXAMPLE 23

A thermostated 1 l glass vessel equipped with a stirrer and a stillhead was charged with 295.4 g of N-methylmorpholine and 220.6 g of water under nitrogen. At internal temperature of 65°–66° C. 175.7 g of 50% strength aqueous hydrogen peroxide solution were added dropwise in the course of 16.5 h. On completion of the addition the mixture was stirred at 65° C. for 5 h. 286 g of NMM/water mixture were distilled off under vacuum of 100 mbar and the remaining bottom product was titrated with 0.5 HCl to determine the NMMO content. It was found to be 66.5%. 145 g of water were added to adjust the content to 50%. The solution had an APHA color number of 108.

We claim:

1. A process for producing aqueous solutions of N-methylmorpholine N-oxide having APHA numbers below 200, based on an N-methylmorpholine N-oxide content of 50% by weight, comprising the steps of:
   A. Obtaining an aqueous N-methylmorpholine solution whose water content is at least 35% by weight;
   B. Oxidizing the aqueous N-methylmorpholine solution with hydrogen peroxide at a temperature range from 50°–80° C.;
   C. Adjusting the concentration of the aqueous N-methylmorpholine N-oxide solution prepared in (B) by distilling off residual N-methylmorpholine and water.

2. A process as claimed in claim 1 wherein the water content of the starting solution of N-methylmorpholine is at least 40% by weight.

3. A process as claimed in claim 1 wherein the water content of the starting solution of N-methylmorpholine is from 35 to 60% by weight.

4. A process as claimed in claim 1 wherein the aqueous N-methylmorpholine starting solution is prepared by admixing distilled N-methylmorpholine with sufficient water for the solution to have a water content of at least 35% by weight, based on the solution.

5. A process as claimed in claim 1 wherein the N-methylmorpholine starting solution is prepared by admixing the steam distillation azeotrope of N-methylmorpholine with sufficient water for the solution to have a water content of at least 35% by weight, based on the solution.

6. A process as claimed in claim 1 wherein N-methylmorpholine and hydrogen peroxide are reacted in a molar ratio of from 1.43:1 to 0.90:1.0.

7. A process as claimed in claim 1 wherein the aqueous hydrogen peroxide solution used is from 30 to 65% strength by weight.

* * * * *